(12) United States Patent
Ruiz Soto et al.

(10) Patent No.: US 9,731,064 B2
(45) Date of Patent: Aug. 15, 2017

(54) MULTI-PORT INTERFACE DEVICE FOR USE WITH MEDICAL FLUIDS

(75) Inventors: Gabriela Maria Ruiz Soto, Monterrey (MX); Jose Isabel Gomez Quinones, Monterrey (MX); Manuel Farias Martinez, Monterrey (MX); Enrique Javier Saldivar Ornelas, Monterrey (MX); Elena Isabel Victoria Quijano Dominguez, Monterrey (MX)

(73) Assignee: INSTITUTO TECHNOLOGICO Y DE ESTUDIOS SUPERIORES DE MONTERREY, Monterrey (MX)

( * ) Notice: Subject to any disclaimer, the term of this patent is extended or adjusted under 35 U.S.C. 154(b) by 854 days.

(21) Appl. No.: 13/265,109

(22) PCT Filed: May 14, 2010

(86) PCT No.: PCT/MX2010/000038
§ 371 (c)(1),
(2), (4) Date: Oct. 18, 2011

(87) PCT Pub. No.: WO2011/002268
PCT Pub. Date: Jan. 6, 2011

(65) Prior Publication Data
US 2012/0143122 A1   Jun. 7, 2012

(30) Foreign Application Priority Data
Jul. 3, 2009  (MX) .................. MX/A/2009/007258

(51) Int. Cl.
*A61M 1/00* (2006.01)
*A61F 13/00* (2006.01)
(Continued)

(52) U.S. Cl.
CPC ..... *A61M 3/0279* (2013.01); *A61F 13/00068* (2013.01); *A61M 1/0088* (2013.01)

(58) Field of Classification Search
CPC ......... A61M 1/00; A61M 27/00; A61F 13/00; A61F 13/02
(Continued)

(56) References Cited

U.S. PATENT DOCUMENTS 4,499,896 A * 2/1985 Heinecke .......... A61F 13/00063
602/47
5,437,651 A    8/1995 Todd et al.
(Continued)

FOREIGN PATENT DOCUMENTS

EP         0355554       2/1990
WO     WO 00/43046    * 7/2000
(Continued)

*Primary Examiner* — Tatyana Zalukaeva
*Assistant Examiner* — Ilya Treyger
(74) *Attorney, Agent, or Firm* — Baker & McKenzie LLP (57) ABSTRACT

An interface device for removing fluid from a surgical site by shaping the interface device in situ to place a set of openings, which are in fluid communication with a connection port adapted for connection to a vacuum source, in contact with at least a portion of the surgical site. This interface device having a connection port with a connection opening for connection to a vacuum source; a multiplicity of openings located on an exterior of the interface device and in fluid communication through the interface device to the connection port so that fluid may be drawn into the openings and removed by vacuum; and the interface device is adapted to allow a set of one or more hands to at least partially conform the interface device to at least a portion of the surgical site to place at least some of the multiplicity of openings in proximity to fluid.

23 Claims, 9 Drawing Sheets

(51) Int. Cl.
 *A61M 3/02* (2006.01)
 *A61M 27/00* (2006.01)
 *A61F 13/02* (2006.01)

(58) Field of Classification Search
 USPC ........... 604/35, 305–308, 317–323, 540–544
 See application file for complete search history.

(56) References Cited

U.S. PATENT DOCUMENTS

| | | | |
|---|---|---|---|
| 6,458,109 B1* | 10/2002 | Henley | A61M 1/0088 604/289 |
| 6,685,681 B2* | 2/2004 | Lockwood et al. | 604/305 |
| 6,903,243 B1* | 6/2005 | Burton | A61F 13/0203 602/41 |
| 8,105,295 B2* | 1/2012 | Blott et al. | 604/315 |
| 8,168,848 B2* | 5/2012 | Lockwood | A61F 13/0203 602/41 |
| 2011/0112492 A1* | 5/2011 | Bharti | A61M 1/0088 604/319 |
| 2012/0046670 A1* | 2/2012 | Engl | A61F 13/00 606/131 |

FOREIGN PATENT DOCUMENTS

| | | |
|---|---|---|
| WO | 03045492 | 5/2003 |
| WO | 2008131895 | 6/2008 |

* cited by examiner

MULTI-PORT INTERFACE DEVICE FOR USE WITH MEDICAL FLUIDS

This application claims priority to and incorporates by reference PCT Application No. PCT/MX2010/000038 which was published as Published Application No. WO 2011/002268 for a Suction Compress. This application claims priority and incorporates by reference the priority document for PCT/MX2010/000038, specifically, Mexican Patent Application No. MX/a/2009/007258 filed Jul. 3, 2009.

BACKGROUND

Field of the Invention

This disclosure relates generally to surgical tools and methods. More specifically, to a device that provides suction for use in removing fluids during surgery or to irrigate a surgical site. For purposes of this disclosure and the claims that follow, a surgical site may be on the skin of a patient, a location or cavity formed during open or minimally invasive surgery, or a naturally occurring cavity such as inside the mouth or other body opening. The term surgical site will typically involve a medical procedure recognized as a form of surgery (including minor procedures conducted at locations other than a hospital) or first responder activities at a battlefield or scene of a car accident. However, for purposes of this disclosure and the claims that follow, a surgical site is any site that has fluids coming from a patient or present because of medical treatment of any type. For purposes of this application and the claims that follow, the term patient is understood to include a human, including a human cadaver, an animal receiving medical care, or a patient simulator such as used to train medical service providers to provide medical services to humans or animals.

During surgery or other medical procedures such as dental procedures, it is useful to remove fluids from the body. These fluids may include blood or other fluids created by the body as well as fluids introduced into the body such as irrigating fluids. Removal of fluids from the body can help reduce the amount of fluid surrounding the portion of the body that is receiving the medical intervention. The removal of fluids may facilitate the medical provider's vision of the portion of the body of interest.

Fluids may be removed from the body by soaking up fluid in gauze or some other material and then removing the gauze soaked with fluid from the body and discarding the gauze.

Fluids may be removed through the use of a sponge. The sponge may be used to remove fluids a number of times rather than just once.

A problem with inserting material including sponges into various portions of a body cavity to absorb fluid is that this process is slow and thus many different pieces of material or sponges are used. It is undesirable, but not unheard of, for gauze or sponges to be left in a body cavity as the cavity is sewn up.

Fluids may be removed from the body by extending a tube into the body and a pressure source below ambient air pressure to pull fluids out of the body. Medical treatment rooms such as operating rooms, hospital rooms, medical offices, or dental offices have vacuum sources for use in removing fluids via tubes. Vacuum pressure can remove a large amount of fluid but only from near the end of the vacuum tube. Thus, the fluids are removed from only one portion of the body unless one of the medical professionals holds the device and moves it from place to place. In many surgical procedures use of one hand of the surgeon to move the suction tube around is undesirable as the surgeon needs to focus on the surgery. Having an assistant move the suction tube from place to place in the body to remove accumulating fluids may be an option but the presence of an extra hand moving around the surgical site interferes with the surgeon's ability to conduct surgery.

Care must be taken when attempting to quickly move the end of the tube from place to place with limited visibility as it is undesirable to make rapid contact with body tissue, particularly organs with the end of the tube or tip of a tube-like head for the suction line. Some suction cannulae while made from flexible material are limited by their tubular shape and thus limited in the ability to conform to the shape of the incision or surgical site. At bare minimum, puncturing or otherwise damaging body organs during the surgery with the movements of the suction line is undesirable.

SUMMARY OF THE DISCLOSURE

Some of the teachings of the present disclosure may be found in an interface device for removing fluid from a surgical site by shaping the interface device in situ to place a set of openings in contact with at least a portion of the surgical site. As the openings are in fluid communication with a vacuum source via channels within the interface device, fluid may be removed from the portion of the surgical site. This interface device may have a connection port with a connection opening for connection to a vacuum source; a multiplicity of openings located on an exterior of the interface device and in fluid communication through the interface device to the connection port so that fluid may be drawn into the openings and removed by vacuum; and the interface device is adapted to allow a set of one or more hands to at least partially conform the interface device to at least a portion of the surgical site to place at least some of the multiplicity of openings in proximity to fluid.

A subset of interface devices before shaping are substantially planar with a first side, an opposite side, and a perimeter between the first side and the opposite side and at least some of the multiplicity of openings are placed on the first side.

A subset of interface devices maintain the fluid communication between at least one of the multiplicity of openings and the connection port with features within the interface device which prevent the first side from contacting the opposite side in reaction to vacuum pressure within the interface device.

Teachings of the present disclosure may be used in a method of removing fluid from a surgical site comprising: connecting a connection port of an interface device to a vacuum source so that suction is applied to a multiplicity of openings on the exterior of the interface device in fluid communication with the connection port; and bending the interface device to at least partially conform to at least a portion of a surgical site to place at least a portion of the multiplicity of openings in proximity to fluid desired to be removed from the surgical site.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The invention can be better understood with reference to the following figures. The components in the figures are not necessarily to scale, emphasis instead being placed upon illustrating the principles of the invention. Moreover, in the figures, like reference numerals designate corresponding parts throughout the different views.

DETAILED DESCRIPTION

Figure 1:
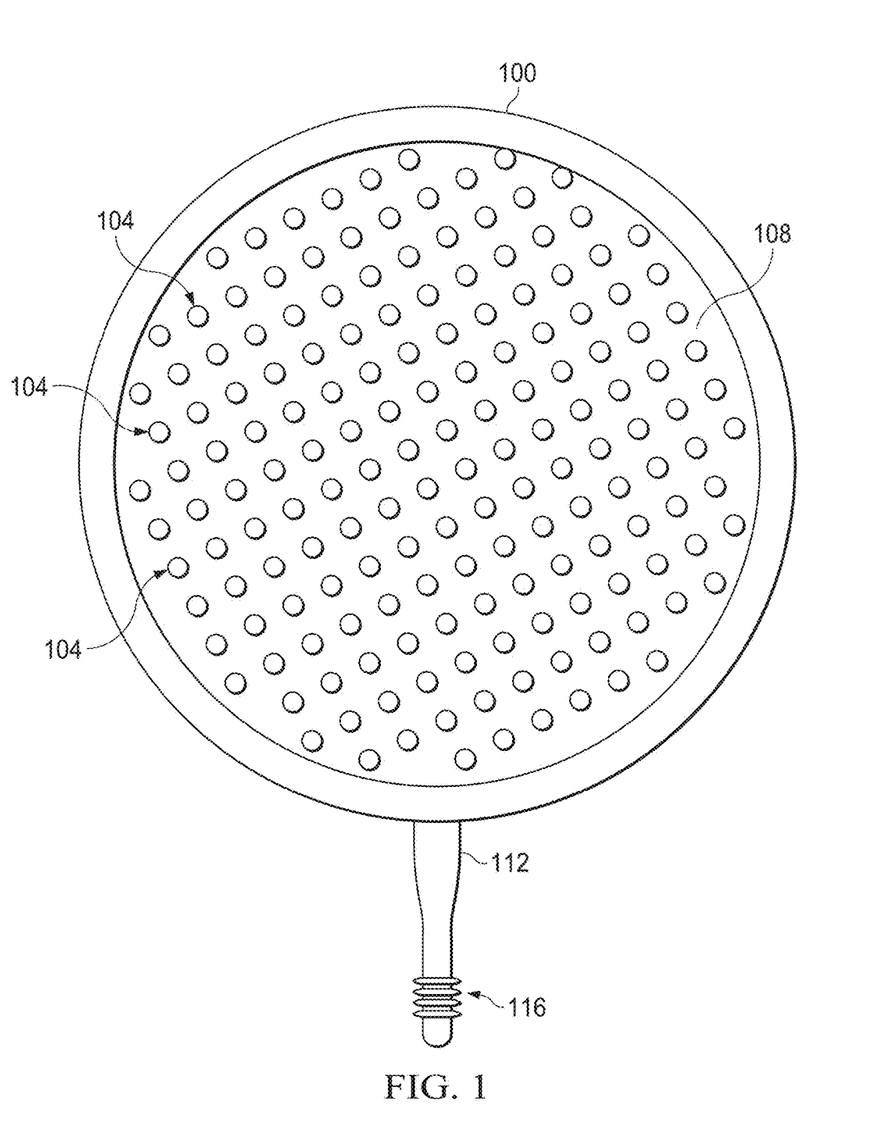
FIG. 1 shows a first side of a multi-port interface device with an array of openings in fluid communication with a connection port.

FIG. 1.

FIG. 1 shows an implementation of the teachings of the present disclosure in a multi-port interface device 100 which can be called an interface device 100. The interface device 100 has an array of openings 104 in an outer layer 108. This array has a multiplicity of openings where multiplicity means a number larger than two but in most instances there will be more than 10 openings.

The size of the holes in the array of openings 104 may be selected based on the anticipated use including the viscosity of the fluid to be moved and the amount of vacuum or pressure to be used. Frequently the hole diameter will be in the range of 0.3 mm to 4 mm.

At the proximal end of the interface device 100 is a connection port 112. In this context, proximal is the end towards the medical service provider and vacuum source or fluid source and distal is the end away from the medical service provider when the device is in its normal orientation.

The proximal end of the connection port 112 has a port connector 116. Any traditional connection may be used for the port connector 116. It is likely that a connection type will be selected that allows for rapid connection and disconnection under surgical conditions, that is easy to manipulate while wearing surgical protective gloves which may have blood or other fluids on the gloves. The particular connector type shown in FIG. 1 is adapted for rapid insertion into appropriately sized flexible tubing.

Figure 2:
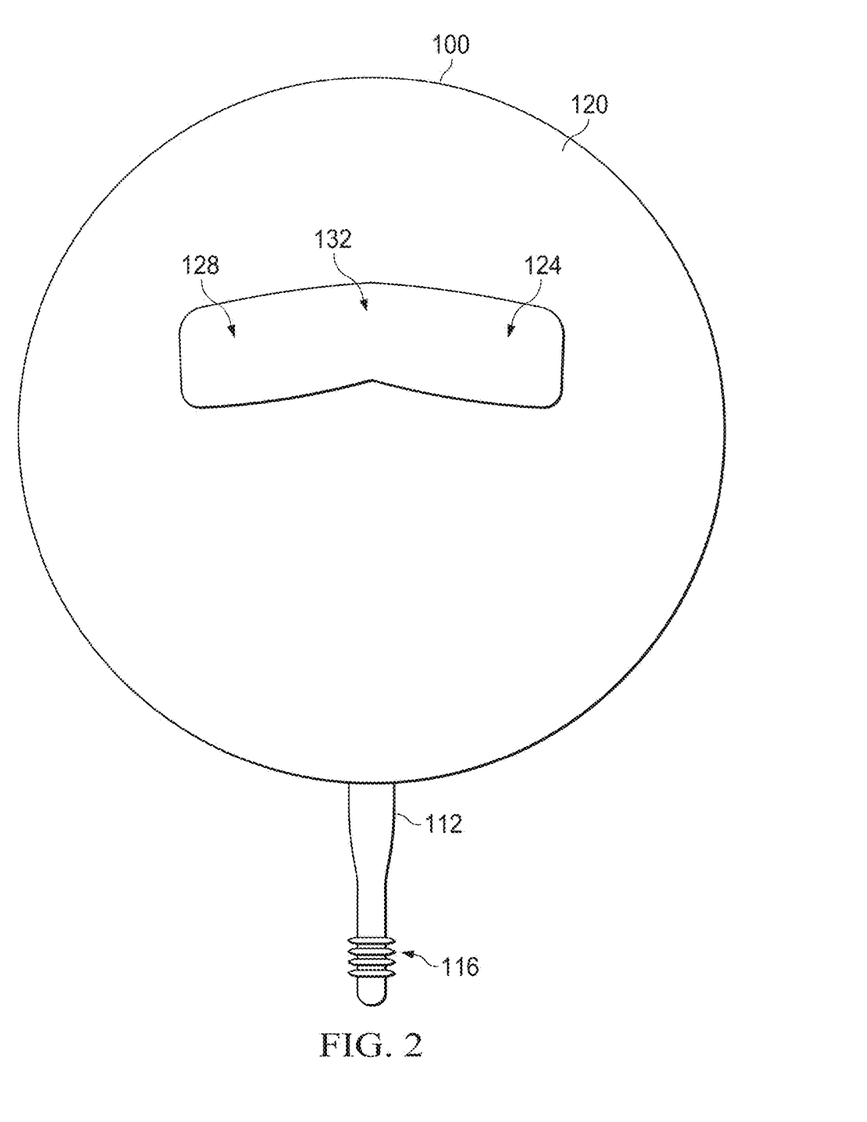
FIG. 2 shows the opposite side of the interface device.

FIG. 2.

FIG. 2 shows the opposite side of the interface device 100. Unlike the outer layer 108, the back side 120 does not have an array of openings. Visible in FIG. 2 is the connection port 112 and the port connector 116. Also visible in FIG. 2 is an optional handle 124. This handle may be implemented in a number of ways but one way is a strap type handle that joins the back side 120 at both ends 128 but has room in the middle portion 132 of the handle 124 to allow several gloved fingers to be inserted between the handle 124 and the back side 120 in order to grab the interface device 100.

Optionally, the connection port 112 may be made of sufficient length and strength that the extended fluid port may be used as a handle for positioning the interface device 100.

Ridges may be included (not shown here) on the outer layer 108 to make it easier to grab the wet device while wearing gloves and to allow the interface device 100 to be used to mildly abrade the surfaces within the surgical site to dislodge material to be removed from the surgical site. These ridges also provide enhanced friction to allow the interface device 100 to stay where it is placed as the interface device is less likely to slip or slide out of position. Ridges may likewise be included on the back side 120 to make the interface device easier to hold and to provide additional friction to keep an interface device in contact with the surgical site where the interface device was placed.

Figure 3:
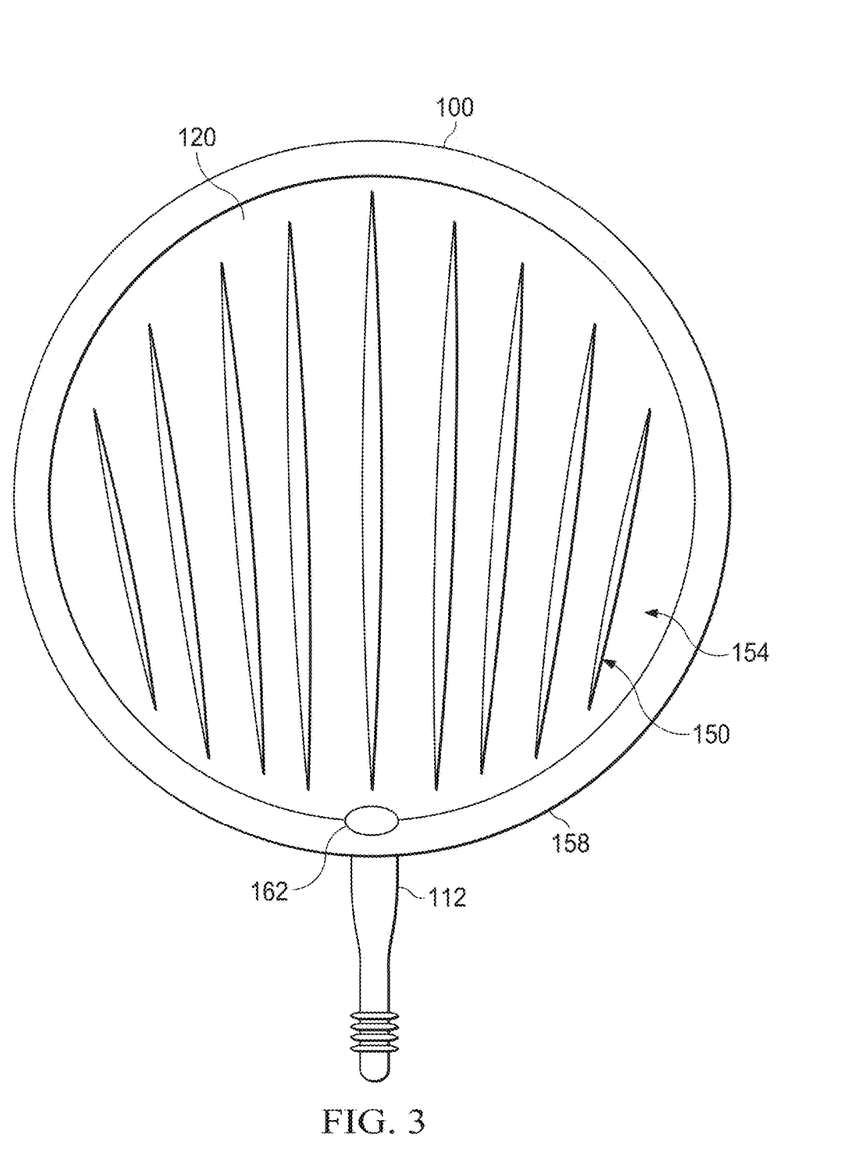
FIG. 3 shows the interior of the interface device.

FIG. 3.

FIG. 3 shows the interface device 100 as shown in FIG. 1, but with the outer layer (108 in FIG. 1) removed. Visible in FIG. 3 are a series of ribs 150 which support the outer layer and maintain separation between the outer layer and inside surface of the back side 120. With the removal of the outer layer, one can see the perimeter 158 of the interface device 100. The areas between the ribs 150 form channels 154 to allow movement of fluid from the array of openings (104 in FIG. 1) to the connection port 112 and to tubing connected to the port connector 116. It is anticipated that the vacuum pressure used with the interface device 100 is going to be in the range of 380 mm of Mercury to 760 mm of Mercury as called for in NFPA 99 Standard for Health Care Facilities (NFPA is the National Fire Protection Association). Atmospheric pressure varies with altitude and weather but standard atmospheric pressure is 760 mm of Mercury (sometimes called 760 torr).

One of skill in the art will appreciate that the precise pattern of the ribs 150 and channels 154 is not critical. A pattern of ribs and channels is suitable for use as long as the outer layer with the array of openings is supported so that the interface device does not collapse inwardly when exposed to a vacuum and as long as the ribs allow adequate channels for fluid to flow to the connection port for suction or from the connection port for irrigation. Generally the ribs will be oriented to be substantially parallel to flow paths from the openings to the connection port.

When the interface device 100 is used for irrigation rather than drainage the fluid path is from the tubing connected to the port connector 116 through the connection port 112 and the channels 154 to and out the array of openings 104.

Although as noted below, there may be some internal clearance between the top of the ribs 150 and the inside of the outer layer, a designer may opt to place all the openings 104 above channels 154 rather than ribs 150.

FIG. 3 includes optional guidance divot 162 (present in FIG. 3 as a small arc at the proximal end of the device perimeter 158). This guidance divot 162 may be useful in some designs to help channel fluids towards the connection port 112. Not all devices will have guidance divot 162.

Figure 4:
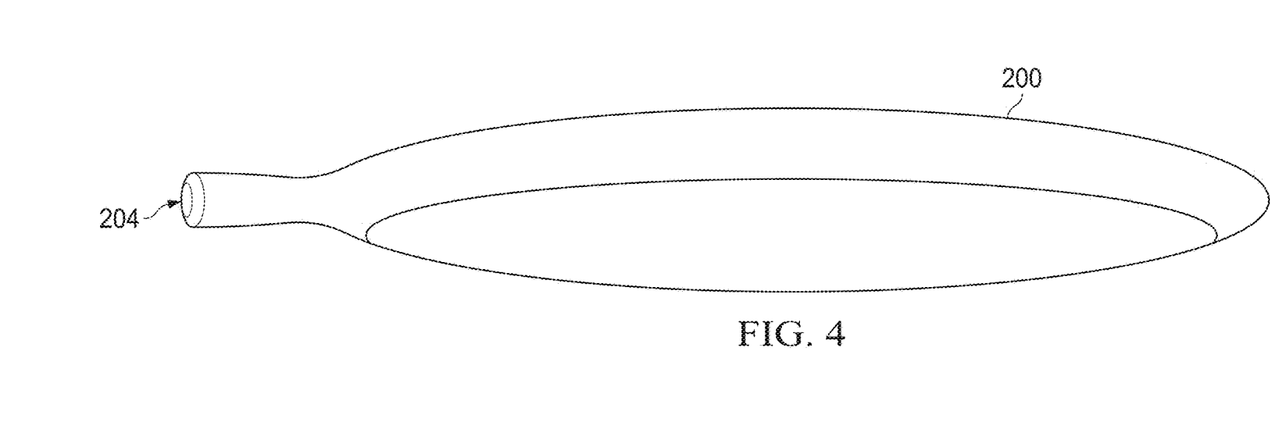
FIG. 4 shows an optional case for the multi-port interface device.

FIG. 4.

As shown in FIG. 4, a cover 200 may be included with some interface devices. The cover 200 would be approximately the same size as the cover 200 would substantially surround the interface device except for an opening 204 to allow interaction between the port connector and the tubing. The cover 200 would be made from a porous material so that fluid could move through the cover 200. The cover 200 could serve as a filter to keep material that might block the openings in the array of openings when the interface device is used to provide suction.

One of skill in the art will recognize that the cover may be made from a range of appropriate porous materials including textiles produced from natural materials, synthetic materials, or some combination of natural and synthetic materials.

Use of the Multi-Port Interface Device for Suction.

Figure 5:
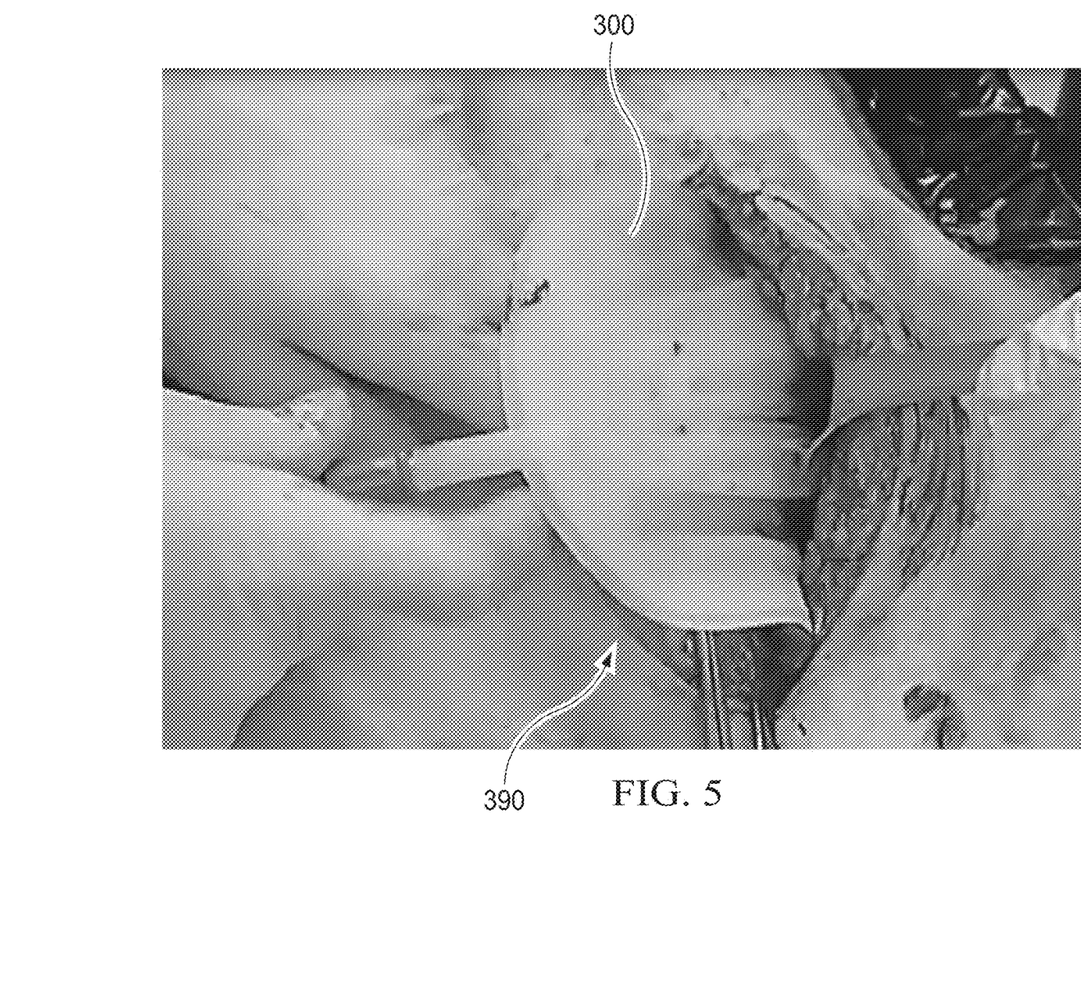
FIG. 5 shows an interface device inserted into a surgical site to provide drainage when the port connector is connected to a tube connected to a vacuum source.

FIG. 5.

An interface device 300 analogous to interface device 100 shown in FIGS. 1-3 may be inserted into a surgical site 390 to provide drainage when the port connector (not visible in FIG. 5 as the gloved hands are holding it) is connected to a tube (not visible in FIG. 5) connected to a vacuum source. The surgical site 390 shown in FIG. 5 is from use of the interface device during surgery on a pig.

Note that the interface device 300 may optionally be made of a partially translucent material so that it is possible to see the presence and movement of fluid in the interface device 300. The partially translucent material may be used for some portions of the interface device with other portions made of substantially opaque material not well adapted to allow monitoring of the movement of fluid.

Note that while at rest, the interface device 300 is substantially planar, the interface device may be made to be substantially flexible to allow the interface device 300 to be bent to have conforming contact to a number of surfaces within the surgical site to allow for removal of fluid from a number of different places.

The interface device 300 may be made sufficiently thin and flexible so that the interface device may be used to wrap around a portion of an organ to allow the medical provider to grab and hold the organ while continuing to remove fluids from the surgical site (or provide a gentle irrigation of the organ).

Note that for some procedures, the interface device 300 may be positioned to remove fluids from the patient or proximity of the patient but other items previously inserted into the surgical site may be between the interface device 300 and the patient. For example, an artificial implant or other equipment may be in a surgical cavity between the interface device and tissue of the patient. These situations are intended to be within the concept of surgical site as the interface device does not need to be placed adjacent to a scalpel in order to be at the surgical site.

One of skill in the art will appreciate that when the interface device 300 is made with the level of flexibility shown in FIG. 5 that care must be taken to keep open the fluid path within the connection port when the interface device 300 is under suction. A stiffening tube may be included within the connection port either as part of the interface device or as a distal extension from the tube that connects to the connection port.

The interface device 300 may be created from a number of biocompatible materials including biocompatible silicon, polyurethane, polyisoprene, and latex.

One of skill in the art will appreciate that having interface devices such shown in FIG. 5 in a variety of diameters will allow a surgeon to have an interface device of an appropriate size for a given surgical procedure based on the normal size of the cavity created during that procedure. Smaller interface devices may be used for a given procedure when done on an infant or small child compared with the same procedure performed on a large adult. The material used in making the interface devices may be tinted to enhance the color contrast between the interface devices and the body parts that are anticipated to be adjacent to the interface devices.

The interface device 300 may have external features that provide mild abrasion to items in the surgical site to dislodge material stuck to portions of the surgical site including clotted blood or even residual adhesive from tape that had been removed.

One of skill in the art can appreciate that an interface device 300 of an appropriate size may be bent to fit into a portion of a surgical site and when the interface device 300 attempts to assume an unbent position, the interface device 300 presses up against portions of the surgical site so that the interface device 300 may be left for an extended period of time without being held by an assistant. Likewise, the interface device 300 can be positioned and held in place by securing the vacuum line leading to the interface device 300. The interface device 300 may be more prone to stay in a particular position if the interface device has surface features to increase the friction between the outside of the interface device and a portion of the surgical site.

One of skill in the art will recognize that in some instances the vacuum source may be connected to the interface device before placement of the interface device adjacent to a portion of the surgical site and in other instances that the vacuum source is connected after placement.

Figure 6:
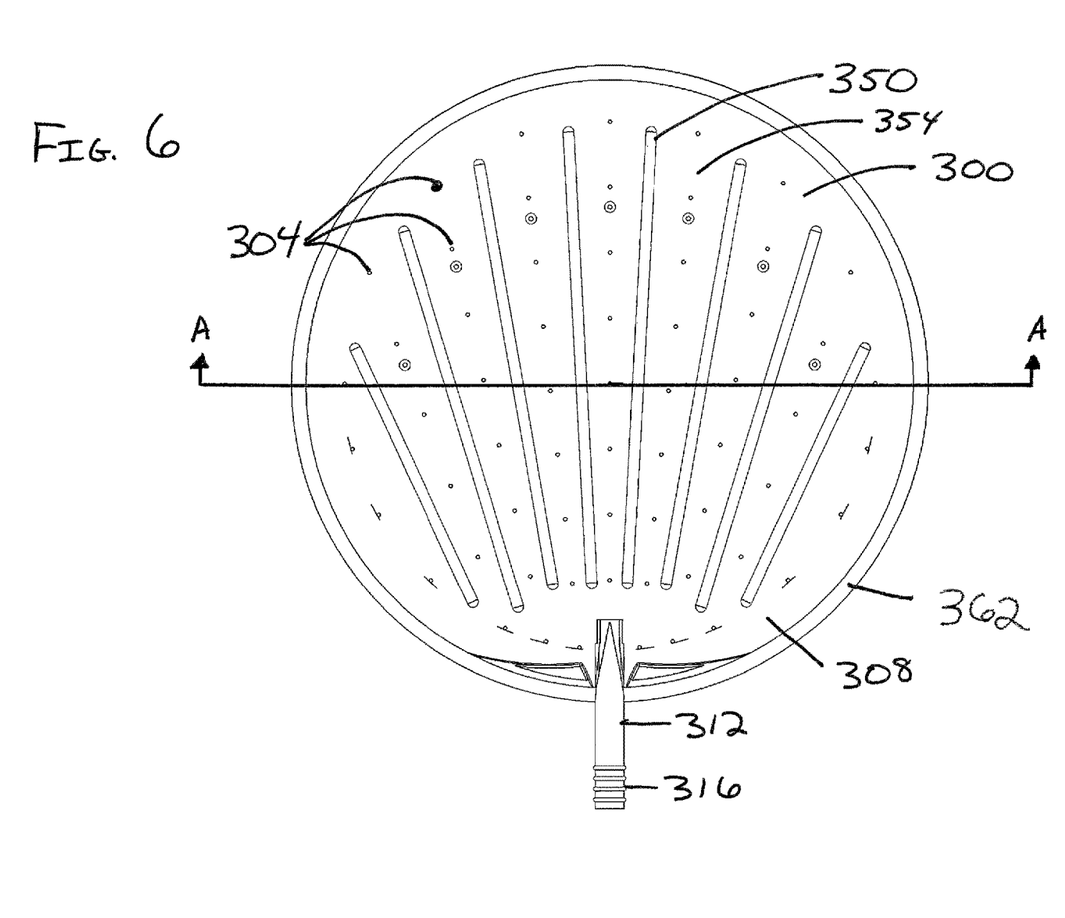
FIG. 6 is a top view of a translucent interface device.

FIG. 6.

FIG. 6 provides details of a translucent interface device 300 like that shown in FIG. 5. FIG. 6 is a top view of interface device 300. The interface device 300 has an array of ports 304 in the top surface 308. A connection port 312 is located at the proximal end of the interface device 300 to provide a fluid communication path between the interior of the interface device 300 and tubing connected to the port connector 316. The connection between the port connector to the tubing may be any reversible connection known for use in connecting medical devices to tubing. The interface device 300 of FIG. 6 does not have a handle analogous to handle 124 shown in FIG. 2.

Figure 7:
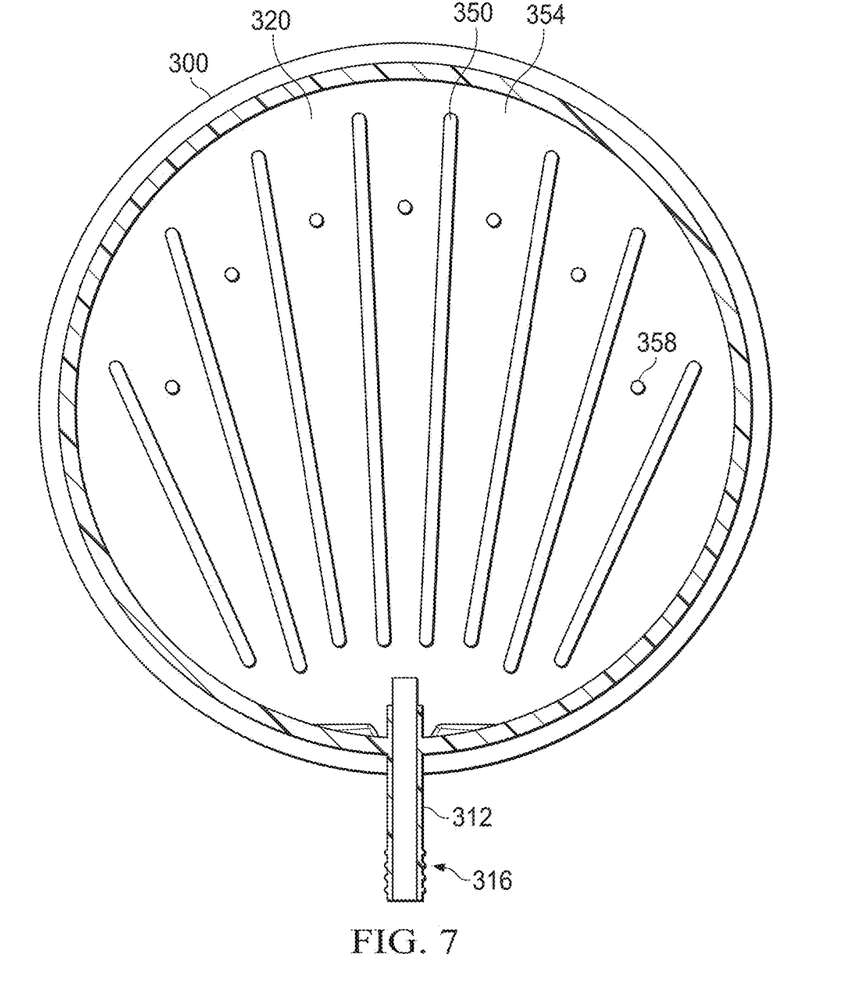
FIG. 7 is a top view of a cross section of FIG. 6.

FIG. 7.

FIG. 7 is a top view of a cross section of FIG. 6. With this cross section, the array of ports 304 and the top surface 308 shown in FIG. 6 are removed. Thus, the wall that is directly visible is the back wall 320. FIG. 7 includes spacers 358 as the spacers 358 work with the ribs 350 to maintain a separation between the interior surface of the back wall 320 and the interior surface of the top surface 308 (FIG. 6) to maintain channels 354. The spacers may be circular as shown here or may be another shape. While the interface device 300 shown in FIG. 7 has only one spacer 358 between each pair of ribs 350, one of skill in the art will recognize that additional spacers 358 to ensure the maintenance of a flow path for fluid even when the interface device 300 is under a vacuum and would thus have a tendency for the malleable walls to collapse inwardly.

One of skill in the art will recognize that for a small interface device (not shown here) or an interface device with a large number of ribs, that the use of spacers 358 may not be necessary.

Figure 8:
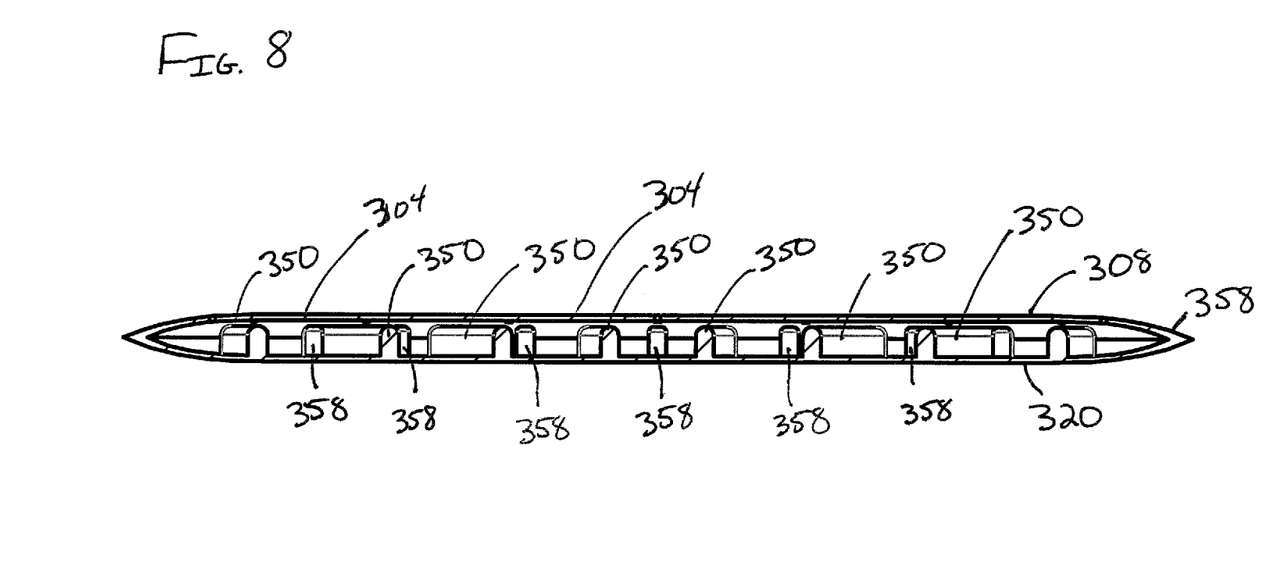
FIG. 8 provides a view of cross section A-A of FIG. 6.

FIG. 8.

FIG. 8 provides a view of cross section A-A of FIG. 6. Visible in FIG. 6 are the top surface 308, the back wall 320 and the perimeter 362. The array of openings 304 are in the top surface 308. The ribs 350 and the spacers 358 extend outwardly from the back wall 320 but are not joined to the top surface 308. One of skill in the art will recognize that the ribs and spacers could be connected to the top surface but not the back wall or may have some features which are connected to one wall and some features connected to the other wall.

Figure 9:
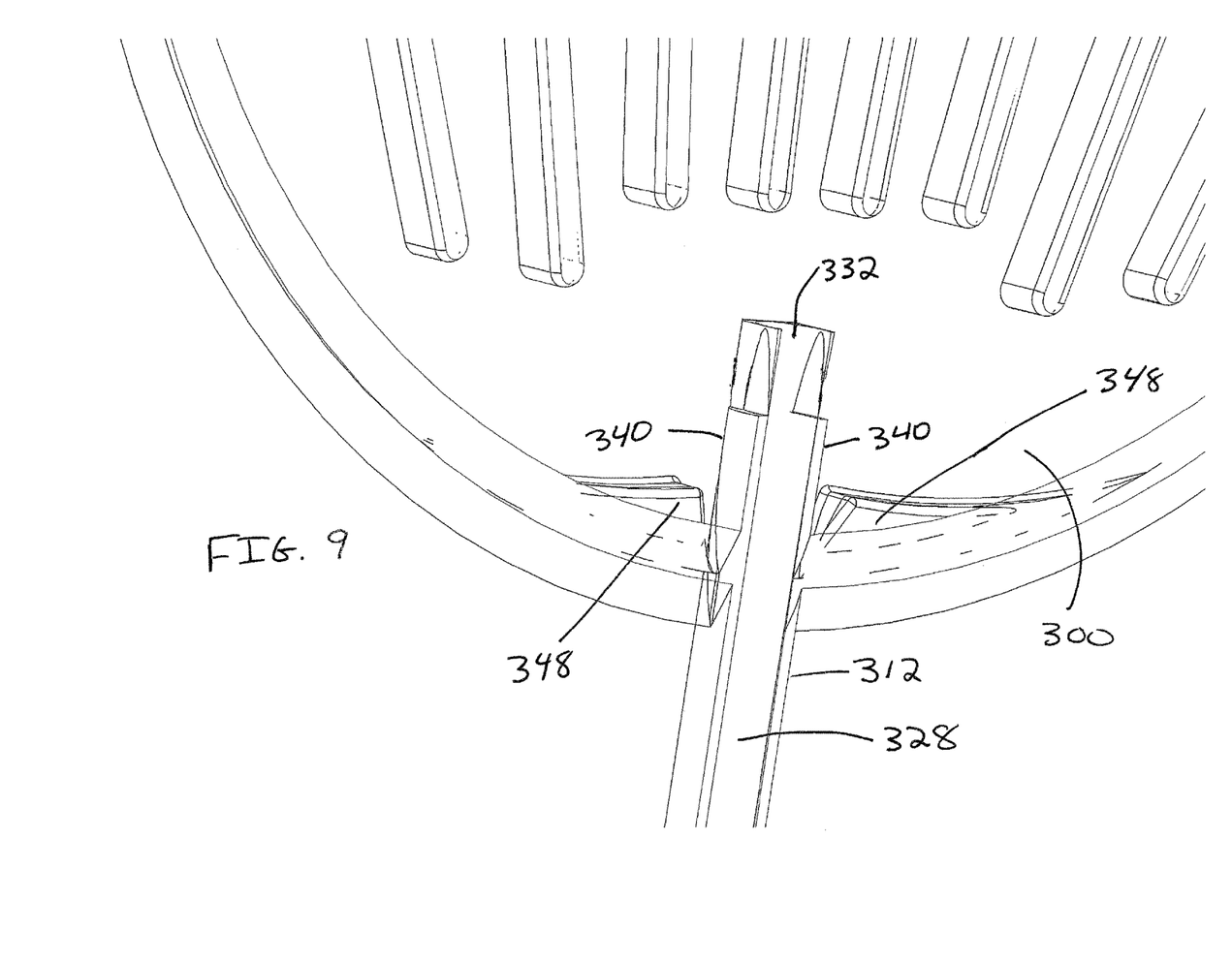
FIG. 9 provides an enlarged and rotated view relative to FIG. 7.

FIG. 9.

FIG. 9 provides an enlarged and rotated view relative to FIG. 7. FIG. 9 provides a view of the distal opening 332 of the fluid communication path 328 within the connection port 312.

FIG. 9 shows reinforcement wall 340 which helps provide additional stiffness to the fluid communication path 328 so that fluid communication path 328 does not collapse as the interface device is bent to conform to a portion of a surgical site.

FIG. 9 also shows ramps 348. These ramps 348 provide additional reinforcement to prevent the device from collapsing when under vacuum. The ramps 348 also prevent fluid from accumulating where the ramps 348 are located.

Alternatives, Variations, and Extensions.

Device with Openings on More than One Side.

The examples set forth above show an interface device with openings on one side and without openings on the back side. One of skill in the art will recognize that the teachings of the present disclosure may be applied to an interface device that has a pattern of openings on both the front and back side of the device. One of skill in the art will need to avoid putting so many openings on the device that the vacuum pressure does not effectively reach enough ports to provide satisfactory fluid removal from the various portions of the surgical site.

Openings Along the Perimeter.

The examples set forth above have the array of openings exclusively in the outer layer. That particular arrangement should not be viewed as a limitation of the range of possible devices. A particular device for use in a particular surgical setting may include openings in the perimeter (See 158 of FIG. 3) of the device as the perimeter will sometimes be the portion of the device inserted into the lowest portion of a surgical site. Thus, an interface device may have openings in the perimeter that are oriented substantially perpendicular to openings on a side of the device.

Non-Uniform Distributions of Openings.

The examples set forth above have the array of openings in a substantially uniform distribution across the outer layer. That particular arrangement should not be viewed as a limitation of the range of possible devices. A designer may design a device that has a greater proportion of openings towards the distal end of the device and fewer towards the proximal end in order to compensate for the less powerful vacuum experienced at the distal openings relative to openings close to the connection port.

Likewise, a designer may choose to have an array of openings with no openings close to the connection port 112 as the connection port 112 will be outside of the surgical site during a certain type of surgery. See for example FIG. 5.

Device without Ribs.

The examples set forth above have ribs or ribs and spacers. One of skill in the art will recognize that a series of spacers may be used without any ribs (150 or 350) as long as the set of spacers is adequate for keeping the device from collapsing while exposed to vacuum pressure and thus interfering with the removal of fluid.

Non-Circular Device.

The examples set forth above show a substantially circular device. One of skill in the art will recognize that the teachings of the present disclosure may be applied to an interface device that has a shape other than substantially circular. The interface device may be a rectangular device (optionally the corners may be rounded on the rectangle). The device may have an unusual shape such as a star and does not need to be symmetric as the device may be tuned for use in a particular procedure and thus has a long section going to one portion of the surgical site and a shorter section or arm going to a different portion of the surgical site. One of skill in the art would be able to adjust the design of the device including the number and width of channels, pattern and size of openings, and other features to obtain the distribution of suction as desired.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

The invention claimed is:

1. An interface device for removing fluid from a surgical site, the interface device comprising:
   a vacuum source;
   a device body having a back side;
   a connection port formed at one end of the back side, the connection port further comprising a connection opening for connection to the vacuum source and a reinforcement wall that prevents the interface device from collapsing under negative pressure;
   a deformable outer layer opposite the device body back side;
   a perimeter between the outer layer and the back side, the perimeter in contact with the outer layer on a first surface of the perimeter such that the outer layer is removably attached to the back side, wherein removal of the outer layer from the back side occurs independently from removal of the connection from the vacuum source to the connection port;
   a multiplicity of openings disposed on the outer layer; the openings being in fluid communication with the vacuum source; and,
   a handle joined to the back side at both ends of the handle, wherein the handle is operable for positioning the interface device within the surgical site;

wherein a plurality of features maintain a separation between the deformable outer layer and the back side when the interface device is connected to the vacuum source, and wherein at least one of an exterior surface of the back side and an exterior surface of the perimeter further comprise a plurality of ridges configured to enhance friction between the interface device and the surgical site.

2. The interface device of claim 1 wherein the device has a substantially circular shape.

3. The interface device of claim 1 wherein the multiplicity of openings are in a substantially uniform distribution exclusively on the outer layer.

4. The interface device of claim 1 further comprising a multiplicity of openings located on the perimeter and substantially perpendicular to some of the multiplicity of openings on the outer layer.

5. The interface device of claim 1 further comprising a multiplicity of openings located on the perimeter.

6. The interface device of claim 1 further comprising a multiplicity of openings located on the back side.

7. The interface device of claim 1 wherein the plurality of features comprises a plurality of ribs.

8. The interface device of claim 7 wherein the plurality of features further comprises:
   at least one spacer protruding from the interior surface of the outer layer towards the interior surface of the opposite side,
   at least one spacer protruding from the interior surface of the back side towards the interior surface of the opposite side, or
   any combination thereof.

9. The interface device of claim 1 wherein the plurality of ridges are operable to mildly abrade at least one surface of the surgical site.

10. The interface device of claim 1 further comprising a porous cover which substantially surrounds the interface device but allows fluid to pass into the interface device after passing through the porous cover and at least one of the multiplicity of openings.

11. The interface device of claim 1 wherein at least a portion of the interface device is sufficiently translucent so that blood removed from the surgical site can be observed moving within the interface device.

12. The interface device of claim 1 further comprising at least one ramp that prevents fluid accumulation and prevents the interface device from collapsing under negative pressure.

13. An interface device for removing fluid from a surgical site, the interface device comprising:
   a vacuum source;
   a device body having a back side;
   a connection port formed at one end of the back side, the connection port further comprising a connection opening for connection to the vacuum source and a reinforcement wall that prevents the interface device from collapsing under negative pressure;
   a deformable outer layer;
   a perimeter between the outer layer and the back side, the perimeter in contact with the outer layer on a first surface of the perimeter such that the outer layer is removably attached to the back side, wherein removal of the outer layer from the back side occurs independently from removal of the connection from the vacuum source to the connection port; and,
   a multiplicity of openings disposed on the outer layer, the openings being in fluid communication with the vacuum source;
      wherein a plurality of features maintain a separation between the deformable outer layer and the back side when the interface device is connected to the vacuum source.

14. The interface device of claim 13 wherein the device has a substantially circular shape.

15. The interface device of claim 13 further comprising a multiplicity of openings located on the perimeter and substantially perpendicular to some of the multiplicity of openings on the first side.

16. The interface device of claim 13 wherein the plurality of features comprises a plurality of ribs.

17. The interface device of claim 16 wherein the plurality of features further comprises:
   at least one spacer protruding from the interior surface of the outer layer towards the interior surface of the opposite side,
   at least one spacer protruding from the interior surface of the back side towards the interior surface of the opposite side, or
   any combination thereof.

18. The interface device of claim 13 further comprising a porous cover which substantially surrounds the interface device but allows fluid to pass into the interface device after passing through the porous cover and at least one of the multiplicity of openings.

19. The interface device of claim 13 wherein at least a portion of the interface device is sufficiently translucent so that blood removed from the surgical site can be observed moving within the interface device.

20. The interface device of claim 13 wherein the multiplicity of openings are exclusively disposed on the outer layer, wherein the diameter of the openings is in a range of 0.3 mm to 4 mm.

21. The interface device of claim 13 wherein the interface device is made of at least one of the following materials: silicon, polyurethane, poly-isoprene, and latex.

22. The interface device of claim 13 wherein the deformable outer layer is made of at least one of the following materials: silicon, polyurethane, poly-isoprene, and latex.

23. The interface device of claim 13 further comprising at least one ramp that prevents fluid accumulation and prevents the interface device from collapsing under negative pressure.

* * * * *

UNITED STATES PATENT AND TRADEMARK OFFICE
CERTIFICATE OF CORRECTION

PATENT NO.            : 9,731,064 B2
APPLICATION NO.  : 13/265109
DATED                : August 15, 2017
INVENTOR(S)        : Gabriela Maria Ruiz Soto et al.

It is certified that error appears in the above-identified patent and that said Letters Patent is hereby corrected as shown below:

On the Title Page

Please change the name of the Assignee (73) by removing the "H" in "TECHNOLOGICO."

In the Claims

In Column 8, Claim 1, Line 62, please change the ";" to a "," between "layer" and "the."

Signed and Sealed this
Twenty-fourth Day of October, 2017

Joseph Matal
*Performing the Functions and Duties of the
Under Secretary of Commerce for Intellectual Property and
Director of the United States Patent and Trademark Office*